United States Patent
Weitzner

(10) Patent No.: US 10,849,683 B2
(45) Date of Patent: *Dec. 1, 2020

(54) ENDOSCOPIC RESECTION METHOD

(71) Applicant: Boston Scientific Scimed, Inc., Maple Grove, MN (US)

(72) Inventor: Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 840 days.

This patent is subject to a terminal disclaimer.

(21) Appl. No.: 15/491,493

(22) Filed: Apr. 19, 2017

(65) Prior Publication Data

US 2017/0215948 A1    Aug. 3, 2017

Related U.S. Application Data

(63) Continuation of application No. 13/325,570, filed on Dec. 14, 2011, now Pat. No. 9,655,671, which is a
(Continued)

(51) Int. Cl.
*A61B 18/12* (2006.01)
*A61B 18/14* (2006.01)
(Continued)

(52) U.S. Cl.
CPC .......... *A61B 18/1482* (2013.01); *A61B 18/14* (2013.01); *A61B 18/16* (2013.01); *A61B 18/1492* (2013.01); *A61B 2017/00269* (2013.01); *A61B 2018/00482* (2013.01); *A61B 2018/00589* (2013.01);
(Continued)

(58) Field of Classification Search
CPC ........... A61B 2018/00482; A61B 2018/00601; A61B 2018/1407; A61B 2018/141; A61B 2017/00269
See application file for complete search history.

(56) References Cited

U.S. PATENT DOCUMENTS 4,311,143 A * 1/1982 Komiya ............. A61B 18/1442
606/47
4,326,530 A    4/1982 Fleury, Jr.
(Continued)

FOREIGN PATENT DOCUMENTS

JP    2000-262536    9/2000

OTHER PUBLICATIONS

Repici, A. and R. Tricerri. Endoscopic polypectomy: techniques, complications and follow-up. Techniques in Coloproctology: [Retrieved from SpringerLink on Jun. 1, 2009] Dec. 2004: vol. 8(2), pp. S283-S290.
(Continued)

*Primary Examiner* — Jaymi E Della
(74) *Attorney, Agent, or Firm* — Bookoff McAndrews, PLLC

(57) ABSTRACT

Embodiments of the invention are directed to a method of excising tissue including injecting fluid into the submucosa to raise targeted tissue. A first electrode is positioned below the targeted tissue within the injected fluid and a second electrode is positioned adjacent a surface of the raised targeted tissue opposite the first electrode. Electrical current is applied between the first and second electrodes and the targeted tissue is excised with the second electrode.

17 Claims, 5 Drawing Sheets

Related U.S. Application Data continuation of application No. 12/848,630, filed on Aug. 2, 2010, now Pat. No. 8,100,905, which is a continuation of application No. 11/210,959, filed on Aug. 25, 2005, now Pat. No. 7,789,881.

(51) Int. Cl.
*A61B 18/16* (2006.01)
*A61B 17/00* (2006.01)
*A61B 18/00* (2006.01)

(52) U.S. Cl.
CPC ........... *A61B 2018/00595* (2013.01); *A61B 2018/00601* (2013.01); *A61B 2018/00982* (2013.01); *A61B 2018/141* (2013.01); *A61B 2018/1407* (2013.01); *A61B 2018/1467* (2013.01); *A61B 2218/002* (2013.01)

(56) References Cited

U.S. PATENT DOCUMENTS

| | | | |
|---|---|---|---|
| 5,961,526 A * | 10/1999 | Chu | A61B 17/32056 606/113 |
| 6,007,546 A | 12/1999 | Snow et al. | |
| 6,063,082 A | 5/2000 | DeVore et al. | |
| 6,123,665 A | 9/2000 | Kawano | |
| 6,221,039 B1 | 4/2001 | Durgin et al. | |
| 6,352,533 B1 | 3/2002 | Ellman et al. | |
| 6,743,228 B2 | 6/2004 | Lee et al. | |
| 6,944,490 B1 * | 9/2005 | Chow | A61B 18/1492 600/374 |
| 2003/0073991 A1 | 4/2003 | Francishelli | |
| 2003/0163129 A1 | 8/2003 | Lee et al. | |
| 2004/0059066 A1 * | 3/2004 | Yamamoto | A61P 41/00 525/418 |
| 2004/0087936 A1 | 5/2004 | Stern et al. | |
| 2005/0096650 A1 | 5/2005 | Ouchi | |
| 2005/0131424 A1 | 6/2005 | Ouchi | |
| 2005/0245927 A1 | 11/2005 | Snay et al. | |
| 2006/0100614 A1 * | 5/2006 | Long | A61B 18/1477 606/27 |
| 2009/0069806 A1 | 3/2009 | De La Mora Levy et al. | |

OTHER PUBLICATIONS

EIC NPL Search enclosed with the Notice of Allowance dated May 27, 2010 in U.S. Appl. No. 11/210,959 (39 pages).

* cited by examiner

ENDOSCOPIC RESECTION METHOD

CROSS-REFERENCE TO RELATED APPLICATIONS

This application is a continuation of U.S. application Ser. No. 13/325,570, filed Dec. 14, 2011, now U.S. Pat. No. 9,655,671, which is a continuation of U.S. application Ser. No. 12/848,630, filed Aug. 2, 2010, now U.S. Pat. No. 8,100,905, which is a continuation of U.S. application Ser. No. 11/210,959, filed Aug. 25, 2005, now U.S. Pat. No. 7,789,881, all of which are incorporated herein by reference in their entireties.

FIELD OF THE INVENTION

Embodiments of this invention relate to methods for removing tissue from a patient. More particularly, at least certain embodiments of the invention relate to methods for endoscopic mucosal resection including injecting fluid into tissue, positioning wire snares at a treatment site, and applying current between the snares in order to cut and remove tissue.

BACKGROUND OF THE INVENTION

Endoscopic methods are commonly used for diagnosis and/or treatment of internal anatomical lumens within a patient's body, such as, for example, the gastrointestinal tract. For example, there are several methods, known as endoscopic mucosal resection, for treating both malignant and non-malignant tumors within a patient's mucosa (the mucous tissue lining various internal anatomical lumens consisting of epithelium, lamina, propria, and, in the gastrointestinal tract, a layer of smooth muscle). Endoscopic mucosal resection may include snaring and then excising sessile adenomas (i.e., tumors attached to a bodily surface) in an anatomical lumen. If the adenoma is flat against the lumen wall, thus making it difficult to snare and excise, one of several methods may be used to raise the flat adenoma so that it may be snared and excised. One method includes using forceps to raise the flat adenoma. Another method includes using a vacuum to raise the flat adenoma. A further method, called hydrodissection includes injecting fluid into the submucosa so as to create a pocket or opening below the tissue to raise the flat adenoma above the underlying tissue.

Once the adenoma is excised, bleeding into the body lumen may result from the underlying portion of the tissue from which the adenoma was removed. These, and other medical procedures (e.g., staining, marking, and identifying tissue), may involve making an incision in body tissue and controlling any consequent bleeding. When performing these procedures, it may be desirable to minimize both tissue trauma during incision and the time required to stop internal bleeding. In addition, it is desirable to cleanly cut and retrieve a uniform tissue sample of sufficient size particularly where a pathology study of the sample is necessary. Furthermore, it is desirable for the resection to leave clean margins at the treatment site in order to minimize any further disruption of the surrounding anatomy.

Minimally invasive or least invasive surgical techniques, such as laparoscopic, endoscopic, or arthoroscopic techniques, are sometimes used because body tissue is usually traumatized less by those techniques than by more invasive conventional techniques. Electrosurgical methodologies, sometimes used in conjunction with the minimally or least invasive techniques, allow the making of an incision and the stopping or stemming of bleeding with less attendant tissue trauma and greater control than do conventional modalities. While useful in stemming the flow of blood resulting from tissue resection, electrosurgical methods can often cause unnecessary burning or trauma beyond the desired treatment site and into the surrounding anatomical lumen wall during a resection procedure.

The aforementioned methods, while effective, have certain drawbacks. As physicians sometimes use different devices to perform different functions, for example, use one catheter to make an incision and another to perform hemostasis or irrigation, the exchange of catheters to provide different functions extends the time to complete therapy, increases the risk to the patient, and also increases patient discomfort. Consequently, physicians have to weigh the time, complexity, and benefits of interchanging single or dual purpose catheters to change treatment modalities against whatever disadvantage may result by working with a single catheter.

Thus, it is desirable to present a method for endoscopic mucosal resection that overcomes the disadvantages of the prior art to, as examples, retrieve a uniform tissue sample adequate for pathology study, maintain clean tissue margins, reduce trauma to the surrounding anatomy, and control the depth of burning attendant to electrosurgery.

SUMMARY OF THE INVENTION

Embodiments of the present invention are directed to methods for removing tissue from a patient. More particularly, at least certain embodiments of the invention relate to methods for endoscopic mucosal resection that obviate one or more of the limitations and disadvantages of prior resection methods.

One embodiment of the invention is directed to a method of excising tissue in a body, comprising injecting fluid into the submucosa to raise targeted tissue and positioning a first electrode below the targeted tissue within the injected fluid. A second electrode is positioned adjacent a surface of the raised targeted tissue opposite the first electrode. Current is then applied between the first and second electrodes and the targeted tissue is excised with the second electrode.

In various embodiments, the method may include one or more of the following additional features: inserting an endoscope into an anatomical lumen of the body, positioning the endoscope proximate the targeted tissue, inserting an injection needle through a working channel of the endoscope to the targeted tissue, and injecting the fluid through the injection needle; wherein the injected fluid raises the targeted tissue through the creation of a fluid pocket within the tissue; wherein the first and second electrodes are not connected; wherein the first and second electrodes are independently moveable; wherein the first electrode is an electrically conductive snare loop; wherein the snare loop is inserted within the injected fluid through an injection needle; wherein the snare loop is movable between a retracted state within a lumen of the needle and an expanded state positioned distally beyond the lumen of the needle; wherein the second electrode is an electrically conductive snare loop; wherein the first and second electrodes are positioned at an excision site through a placement catheter having first and second lumens housing the first and second electrodes; wherein the first and second electrodes are electrically conductive snare loops, each snare loop being movable between a retracted state and an expanded state; wherein current is applied between the first and second electrodes, such that one of the first electrode and the second electrode is an active electrode and the other of the first electrode and the second electrode is a return electrode in a bipolar circuit; wherein the snare loop is movable within an insulating lumen between a retracted state and an expanded state, the method further comprising selecting the amount of conductive snare loop to expose in order to control a current applied to the targeted tissue; wherein the snare loop is movable within a lumen of a medical device between a retracted state and an expanded state such that the snare loop excises the raised targeted tissue upon retraction of the snare loop into the lumen; wherein applying current coagulates tissue; wherein the injected fluid is a non-ionic fluid; wherein attracting magnets are disposed on each electrode such that the electrodes align when positioned.

Another embodiment of the invention is directed to a method of excising tissue in a body, comprising injecting an electrically conducting fluid below targeted tissue and positioning an electrode adjacent a surface of the targeted tissue opposite the electrically conducting fluid. A conductor is positioned below the targeted tissue to contact the electrically conducting fluid. Current is applied between the electrically conducting fluid and the electrode and the targeted tissue is excised with the electrode.

In various embodiments, the method may include one or more of the following additional features: wherein the fluid is a conductive gel; wherein the electrode is an electrically conductive snare loop; wherein the snare loop is housed within a flexible sheath and is movable between a retracted state within a lumen of a sheath and an expanded state positioned distally beyond the lumen of the sheath; inserting an endoscope into an anatomical lumen of the body; positioning the endoscope proximate the targeted tissue; and inserting an injection needle through a working channel of the endoscope to the targeting tissue; and injecting the electrically conducting fluid through the injection needle; wherein an injection needle for injecting the fluid is positioned proximate the targeted tissue through a first lumen of a placement catheter and the electrode is positioned through a second lumen of the placement catheter, wherein current is applied between the electrically conducting fluid and the electrode, such that one of the fluid and the electrode is an active electrode and the other of the fluid and the electrode acts as a return electrode in a bipolar circuit; wherein the snare loop is movable within an insulating lumen between a retracted state and an expanded state, the method further comprising selecting the amount of conductive snare loop to expose in order to control the current applied to the targeted tissue; wherein the snare loop is movable within a housing lumen of a medical device between a retracted state and an expanded state such that the snare loop excises the targeted tissue upon retraction of the snare loop into the lumen; wherein applying current coagulates tissue; wherein the injected conductive fluid raises the targeted tissue through the creation of a fluid pocket within the tissue; wherein the conductive fluid is injected into the submucosa to raise the target tissue.

Another embodiment of the invention is directed to a method of excising tissue in a body, comprising inserting a first snare loop below targeted tissue and positioning a second snare loop adjacent a surface of the targeted tissue opposite the first snare loop. Current is applied between the first and second snare loops and tissue is excised with the second snare loop.

In various embodiments, the method may include one or more of the following additional features: wherein the second snare loop is not connected to the first snare loop; wherein the first and second snare loops are independently moveable; injecting fluid into the submucosa below the targeted tissue to raise the targeted tissue and positioning a first electrode below the targeted tissue within the injected fluid; positioning the endoscope proximate the targeted tissue; inserting an injection needle through a working channel of the endoscope to the targeted tissue; and injecting the fluid through the injection needle; wherein each of the first and second snare loops are movable within separate lumens of a medical device between retracted and expanded states such that the snare loops may excise the raised targeted tissue upon retraction of a snare loop into a lumen; wherein current is applied between the first and second snare loops, such that one of the first and the second snare loops is an active electrode and the other of the first and second snare loops is a return electrode in a bipolar circuit.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Figure 1A:
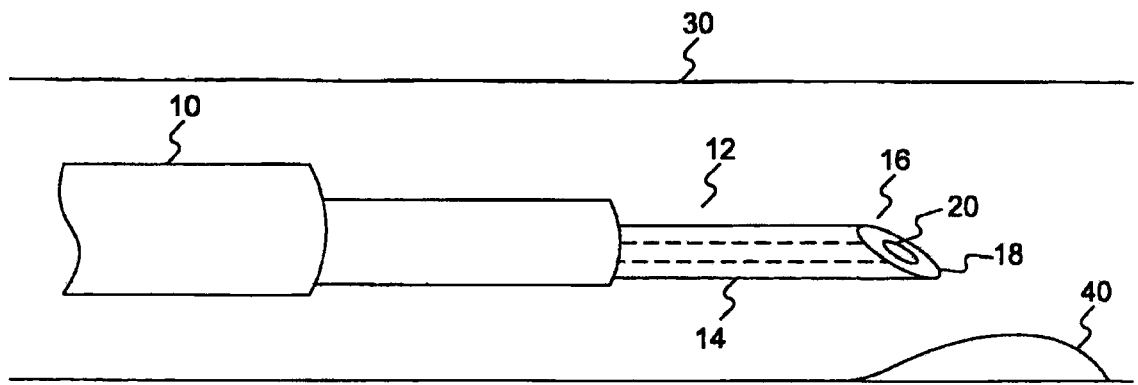
FIG. 1A illustrates the placement of an injection needle through an endoscope into an anatomical lumen with an adenoma, according to an embodiment of the invention.

FIG. 1A illustrates an endoscope 10 positioned within a patient's anatomical lumen 30 for the treatment of a sessile adenoma 40. An injection needle 12 is positioned within the anatomical lumen 30 through a working channel of the endoscope 10. The injection needle 12 includes a shaft 14, a piercing tip 16 having a bevel 18 and an opening 20 at its distal end (i.e. the end further from the operator during use). During endoscopic treatment procedures, injection needles are often used, for example, to introduce irrigation fluids at a treatment site, inject vaso-constrictor fluid into a vessel to slow hemorrhaging, or inject a sclerosing agent to control bleeding varices by hardening the targeted tissue.

Figure 1B:
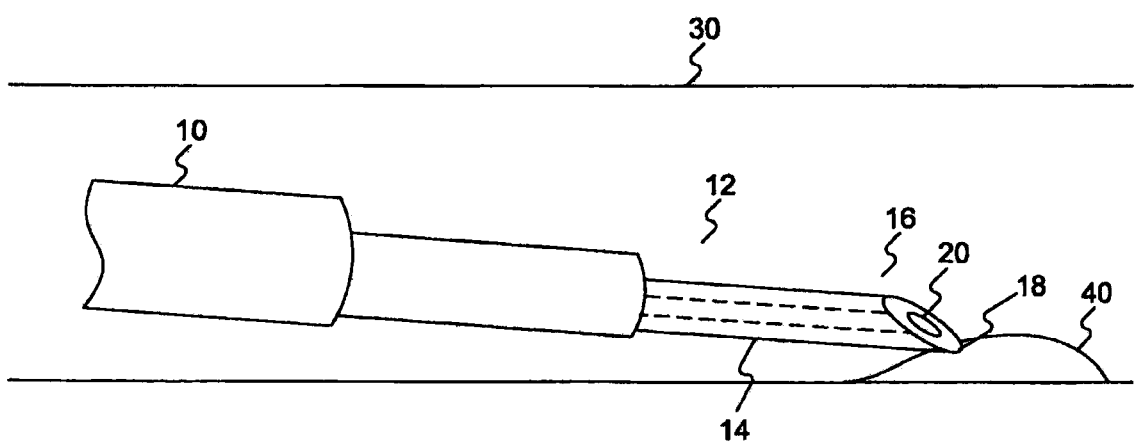
FIG. 1B illustrates an injection needle piercing the tissue below an adenoma within an anatomical lumen, according to an embodiment of the invention.
Figure 1C:
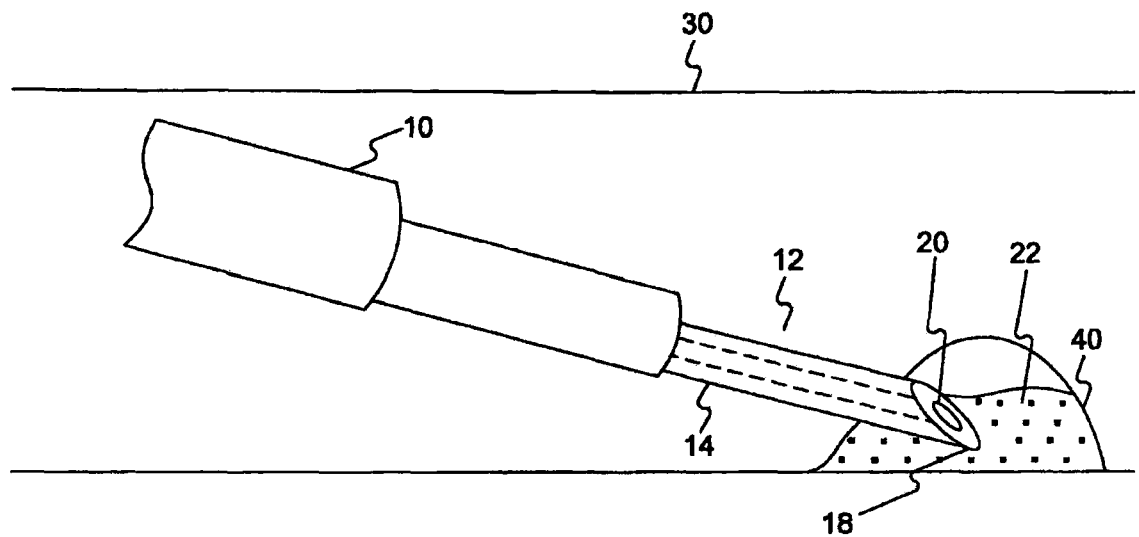
FIG. 1C illustrates an injection needle infusing fluid into the tissue below an adenoma within an anatomical lumen, according to an embodiment of the invention.
Figure 2:
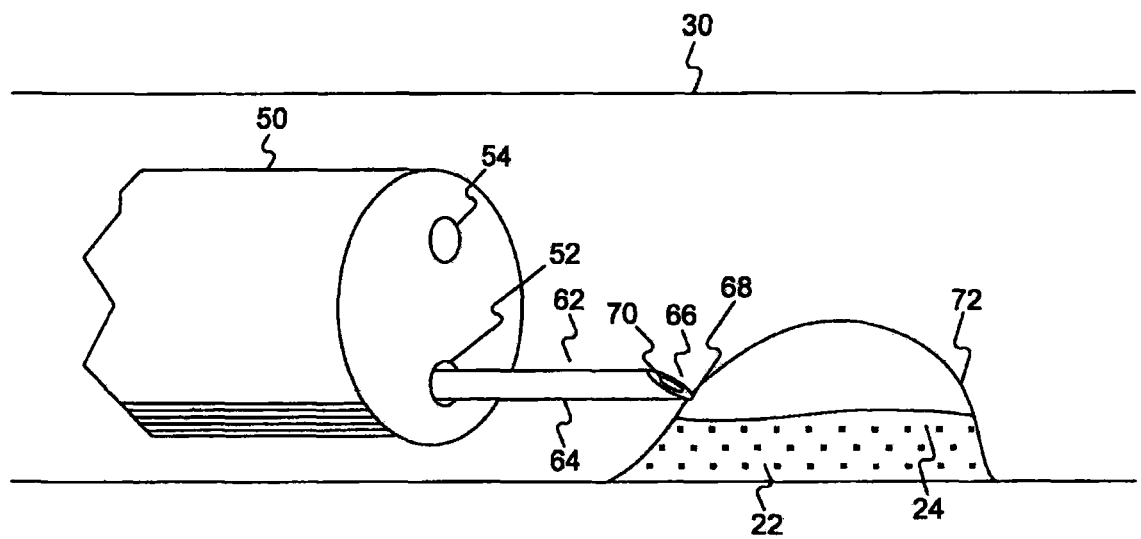
FIG. 2 illustrates a placement catheter positioning another injection needle within the anatomical lumen of a patient, according to an embodiment of the invention.

Referring to FIG. 1B, the endoscope 10 housing the injection needle 12, is positioned at the site of the sessile adenoma 40. The needle 12 is positioned such that the bevel 18 of the piercing tip 16 is inserted into tissue at the base of the adenoma 40. FIG. 1C illustrates a hydrodissection procedure within the anatomical lumen 30. During hydrodissection, temporary bulking of tissue occurs by the injection of fluid at a tissue treatment site to separate certain tissue layers. In the present method, hydrodissection of tissue is performed in order to facilitate the snaring and excision of an adenoma by injecting fluid into the submucosa so as to create a pocket or opening below the tissue to raise the flat adenoma above the underlying tissue. As seen in FIGS. 1C and 2, after the bevel 18 pierces the adenoma 40, injection fluid 22 is infused at the base of the adenoma 40 along the anatomical lumen 30.

During hydrodissection, a bolus of sterile solution is injected into the tissue, resulting in an opening or fluid pocket 24. The volume of fluid injected into the tissue in the hydrodissection procedure is too large to be rapidly absorbed such that the tissue must separate to accommodate the fluid. In the present invention, the injection needle 12 preferably creates a fluid pocket 24 by injection of a fluid 22 into the desired treatment site to lift the resection target. Examples of specific fluids include, but are not limited to, hydrooxypropyl methyl cellulose, hyaluronic acid, or saline (which may also include epinephrine). Because the injected fluid 22 is not immediately absorbed, the fluid pocket 24 creates a raised adenoma 72.

Figure 3:
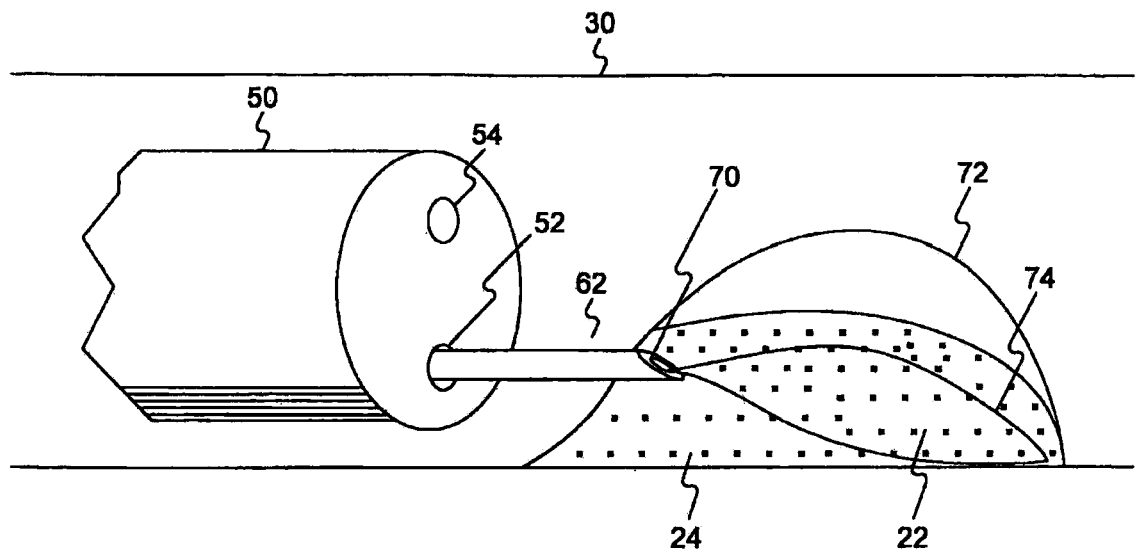
FIG. 3 illustrates positioning a snare loop within a fluid pocket formed below an adenoma within an anatomical lumen, according to an embodiment of the invention.

FIG. 2 shows a placement catheter 50 including a first lumen 52 and a second lumen 54. As illustrated, the first lumen 52 houses an injection needle 62 including a shaft 64, a piercing tip 66 having a bevel 68 and an opening 70 at its distal end. The catheter 50 is positioned in order to allow the injection needle 62 to reach the raised adenoma 72. Referring to FIG. 3, the injection needle 62 is positioned so as to pierce the raised adenoma placing the opening 70 of the needle 62 within the fluid pocket 24 previously created by injection needle 12 of FIGS. 1A-1C.

In an alternative embodiment, the hydrodissection could be performed using positioning catheter 50 and infusing the injection fluid 22 through needle 62. Such an arrangement obviates the need for the separate injection needle 12.

Referring again to FIG. 3, the injection needle 62 houses an electrically conductive snare loop 74 within the internal lumen of the needle shaft 64. The snare loop 74 is capable of being moved between a retracted state within the lumen of the needle 64 and an expanded state positioned distally beyond the opening 70 of the needle. The snare loop 74 may be formed of any material capable of conducting electricity and suitable for resilient movement between expanded and retracted states. Exemplary materials include, but are not limited to, stainless steel and nickel titanium alloys commonly referred to as nitinol.

As illustrated in FIG. 3, once the opening 70 of the injection needle 62 is positioned within the fluid pocket 24, the electrically conductive snare loop 74 is extended outside the needle opening 70 and placed within the fluid pocket 24. The electrically conductive snare loop 74 may be connected at its proximal end (i.e. the end closer to the operator during use) to a source of high frequency current (not shown) capable of energizing the snare loop 74 to act as a electro-surgical treatment electrode upon the activation of the current source. Snare loop 74 also may be connected to any suitable actuator (such as a wire) that extends through needle 62 to a proximal end of the device. The actuator may connect to any suitable handle at the proximal end that is used to extend and retract snare loop 74 relative to needle 62. The actuator also may conduct electric current to loop 74 and connect at the proximal end to a source of electric current.

Figure 4:
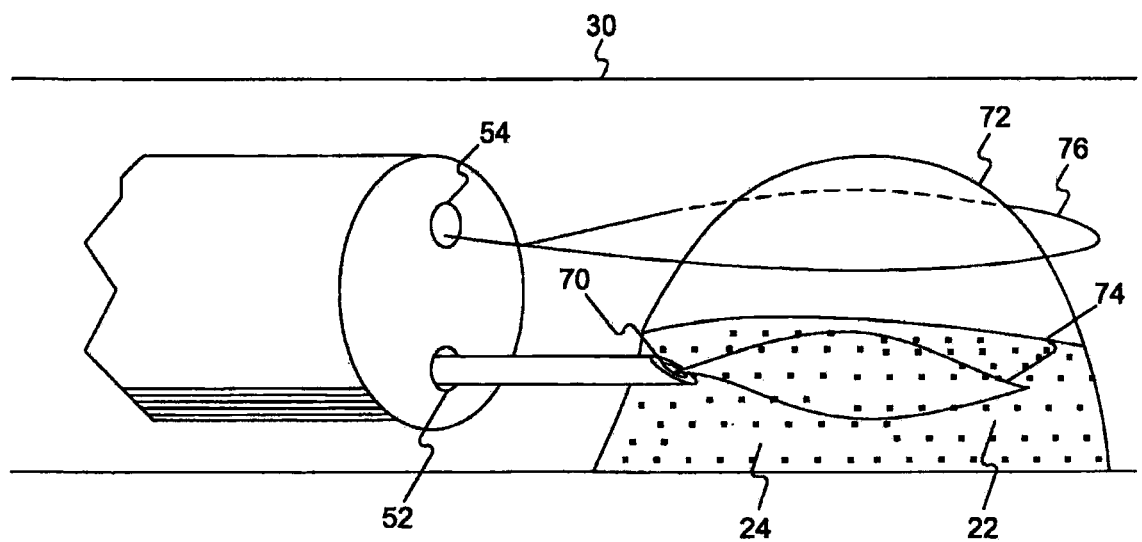
FIG. 4 illustrates the placement of first and second snare loops within an anatomical lumen, according to an embodiment of the invention.

Referring to FIG. 4, the second lumen 54 of the placement catheter 50 houses a second electrically conductive snare loop 76. The second snare loop 76 is capable of being moved between a retracted state within the second lumen 54 and an expanded state positioned distally beyond catheter 50. FIG. 4 illustrates the second electrically conductive snare loop 76 in the expanded state distally beyond the second lumen 54 of catheter 50 and positioned to surround an upper outside surface of the raised adenoma 72. Just as described above with regard to the first snare loop, the second snare loop 76 may be formed of any material capable of conducting electricity and suitable for resilient movement between expanded and retracted states. Exemplary materials include, but are not limited to, stainless steel and nickel titanium alloys commonly referred to as nitinol. In addition, the electrically conductive snare loop 76 may also be connected at its proximal end to a source of high frequency current (not shown) capable of energizing the second snare loop 76 to act as a electrosurgical treatment electrode upon the activation of the current source. And, snare loop 76 may be connected to an actuator wire extending through lumen 54 to a proximal handle. The first and second snare loops 74, 76 are independently movable relative to each other for proper placement at the desired treatment site.

In the resection method according to an embodiment of the current invention, high frequency current is applied, thorough the use of a source of high frequency power source (not shown), to flow between the first electrically conductive snare 74 and the second electrically conductive snare 76. The current can be applied such that the first and second snares act as first and second bipolar electrodes, with one snare acting as the active electrode and the other acting as the return electrode to complete a bipolar electrosurgical circuit. Upon the application of current between the first and second electrically conductive snares 74 and 76, the raised adenoma 72 can be excised upon the tightening, or closing, of the second snare loop 76 through retraction proximally within the second lumen 54 of the catheter 50. The current flowing between the first and second snares provides sufficient energy to assist in cutting through the target tissue while acting to coagulate and/or cauterize the underlying tissue site along the anatomical lumen 30.

Alternatively, only one of the electrically conductive snares 74, 76 may be connected to a source of current. In such a configuration, the one electrically conductive snare would act as a monopolar electrode to assist in cutting through the target tissue while acting to coagulate and/or cauterize the underlying tissue site along the anatomical lumen 30. The current flowing from the monopolar snare electrode would return to the current source and complete the electric circuit through, for example, a patient ground return electrode often positioned externally on the patient's back.

The catheter 50 is preferably formed of a non-conducting polymer material. Similarly, injection needle 62 may be formed with a coating of an insulating polymer material incapable of conducting electricity. Accordingly, the flow of current between the first and second electrically conductive snares 74,76 can be altered by an operator controlling the amount of exposed area of the electrically conductive snare 74,76 beyond the insulating materials of needle 62 and catheter 50. Because both electrically conductive snares 74 and 76 can be selectively movable between retracted and expanded states, the operator can precisely control the amount of exposed conductive material serving to pass current between the snares 74,76.

Depending on such factors as the type of tissue targeted for resection, the impedance of the injection fluid 22, and the desired effect on treatment tissue, the operator may change the direction of current flow between the first and second electrically conductive snares 74,76. For example, the operator may choose, depending on the treatment procedure, to modify the flow of current such that in one operation, the first electrically conductive snare 74 acts as the active electrode in the bipolar circuit, and later in another operation the second electrically conductive snare 76 acts as the active electrode in the bipolar circuit. Such versatility allows the operator to more precisely affect the current flow through the targeted tissue and to control the resulting effect at the treatment site.

Figure 5:
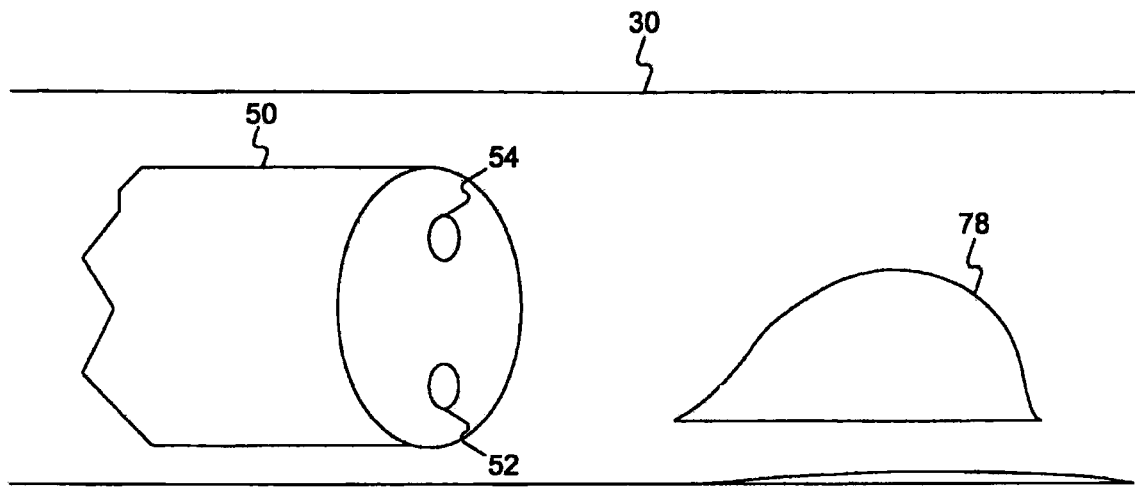
FIG. 5 illustrates a placement catheter within an anatomical lumen of a patient after the completion of a resection procedure, according to an embodiment of the invention.

Referring to FIG. 5, after the mucosal resection procedure, the first and second electrically conductive snares 74 and 76 are moved to their respective retracted states. In addition, the injection needle 62 is also withdrawn proximally into the first lumen 52 of the placement catheter 50 and withdrawn from the anatomical lumen 30 outside of the patient. The resected adenoma 78 can then be captured with a separate retrieval instrument if pathology study of the tissue sample is necessary.

Figure 6:
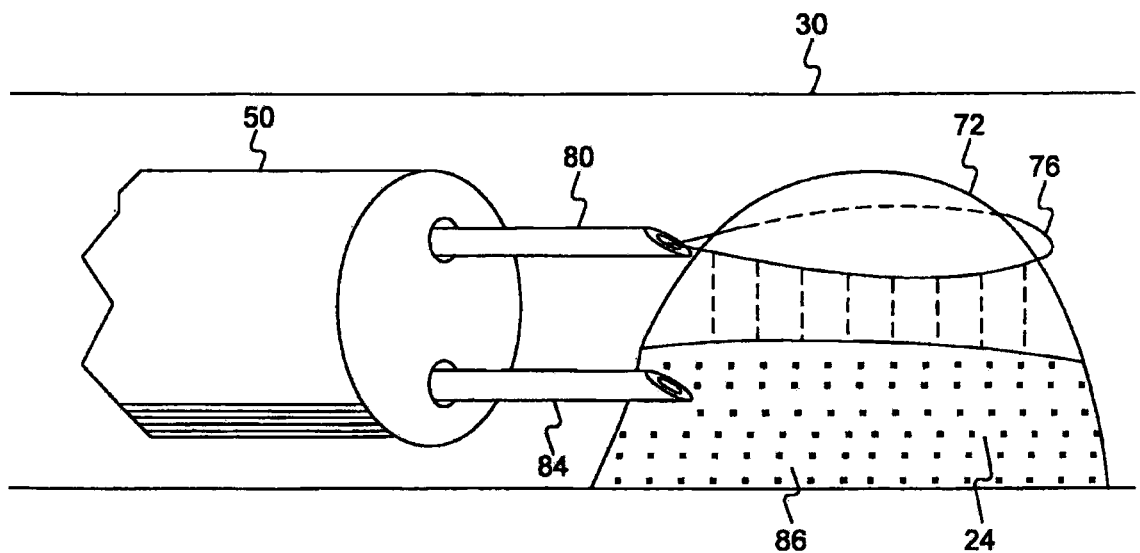
FIG. 6 illustrates an alternative resection procedure, according to an embodiment of the invention.

FIG. 6 depicts an alternative method according to an embodiment of the present invention. Placement catheter 50 is illustrated as positioned at a desired treatment site within an anatomical lumen 30. FIG. 6 differs from the prior embodiment in that the injection fluid infused to create the fluid pocket 24 is an electrically conductive fluid or gel 86. In this embodiment, an injection needle similar to the injection needle 12 of FIG. 1 can positioned to extend within the fluid pocket 24 and act as a first electrode in the application of high frequency current during the resection procedure. Alternatively, a simple flexible conductor 84, such as, for example, a conducting wire capable of being extended into the tissue pocket 24, may be used to connect the conductive fluid or gel 86 to a source of high frequency current. Conductor 84 may also serve as an additional resection tool during a treatment procedure.

In addition, the second lumen 54 of the placement catheter 50 may include a flexible sheath 80 that houses the electrically conductive snare loop 76. The flexible sheath 80 may facilitate more accurate positioning of the snare loop 76 at the treatment site. In the embodiment of FIG. 6, current is passed between the conductive gel 86 and the snare loop 76 to provide sufficient energy to assist in cutting through the target tissue while acting to coagulate and/or cauterize the underlying tissue site along the anatomical lumen 30. The use of conductive fluid or gel is advantageous in that is can serve the dual purposes administering hydrodissection and acting as an electrode during the application of high frequency current.

Figure 7:
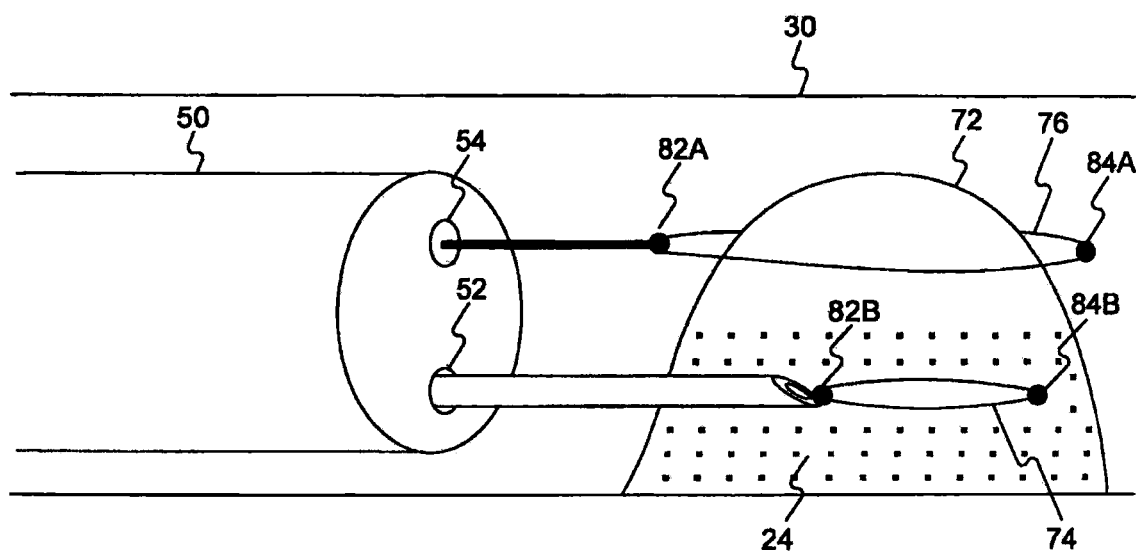
FIG. 7 illustrates another alternative resection procedure, according to an embodiment of the invention.

FIG. 7 depicts an additional feature according to an embodiment of the present invention. FIG. 7 illustrates an endoscopic mucosal resection procedure for excising a raised adenoma 72, include a placement catheter 50 and first and second electrically conductive snare loops 74,76. In order to facilitate proper alignment between electrodes, the snare loops 74 and 76, which act as the first and second electrodes in a bipolar circuit, include an alignment mechanism. In one embodiment, magnets 82A-82B and MA-84B are provided along the first and second snare loops 74,76. FIG. 7 depicts the first conductive snare loop 74 positioned within the fluid pocket 24. The pair of magnets 82A and 82B are magnetically attracted toward each other in order to align the proximal ends of the first and second snares 74 and 76 in order to more precisely position the electrodes.

In addition, another pair of magnets MA-MB are provided along the distal portion of the first and second snares 74 and 76. The pair of magnets 84A and 84B are magnetically attracted toward each other in order to align the distal ends of the first and second snares 74 and 76 in order to more precisely position the electrodes during a resection procedure. While the embodiment shows a pair of magnets associated with each snare loop, more or less magnets may be used. In addition, the magnets may be positioned at other locations along the snare loop.

Alternative alignment mechanisms can be used in place of the magnet embodiments described above. For example, alignment could be achieved with markers on the proximal end of the device indicating how much of each snare surface has been deployed. Furthermore, radiopaque markers could replace the magnets described above. In such an embodiment visualization techniques such as, x-ray, MRI, fluoroscopy, and endoscopic visualization could be performed to achieve proper alignment of the snares. Additionally, various electronic transducers could be disposed in place of, or in addition to, the magnets described above. For example, piezoelectric transducers could be disposed along the snares to control movement and bending of the snare to aid in alignment and positioning of the snare loops. Another arrangement includes the use of photo-detector and photo-emitter transducers disposed along the corresponding portions of the snare loops in order to provide feedback to a user regarding the relative positioning and alignment of the snare loop structure.

It is to be understood that any feature described with reference to a particular figure or embodiment may be repeated in and utilized in any of the other embodiments or figures disclosed in this application. For example, it is intended that any embodiment may include the use of aligning magnets and the first and second snares.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of resecting targeted tissue, comprising:
   injecting fluid to raise the targeted tissue;
   extending one of a first electrically conductive snare or a second electrically conductive snare distally of an injection needle housed within the catheter and into the targeted tissue, wherein the injection needle includes an insulation coating;
   passing current between the first electrically conductive snare and the second electrically conductive snare;
   adjusting an amount of the current passed between the first and second electrically conductive snares by moving at least one of the first and second electrically conductive snares relative to a catheter; and
   resecting the targeted tissue.

2. The method of claim 1, further including positioning at least one of the first and second snares around the targeted tissue.

3. The method of claim 1, further including positioning at least a portion of the injection needle within the raised targeted tissue.

4. The method of claim 3, further including positioning another of the at least one of the first or second snares around the raised targeted tissue.

5. The method of claim 1, wherein the first and second snares form a bipolar circuit.

6. The method of claim 1, further including aligning an alignment mechanism of the first snare relative to an alignment mechanism of the second snare.

7. The method of claim 1, wherein the targeted tissue is submucosal tissue.

8. A method of resecting targeted tissue, comprising:
   injecting fluid into submucosa to raise the targeted tissue via an injection needle, wherein the injection needle includes an insulation coating;
   extending a first electrode through the injection needle and into the targeted tissue;
   positioning a second electrode about a surface of the raised targeted tissue opposite the first electrode;
   passing current between the first and second electrodes;
   adjusting an amount of the current passed between the first and second electrodes by moving at least one of the first or second electrodes relative to another of the first or second electrodes; and
   resecting the targeted tissue.

9. The method of claim 8, further including aligning an alignment mechanism of the first electrode relative to an alignment mechanism of the second electrode.

10. The method of claim 8, wherein the first electrode includes an electrically conductive snare loop.

11. The method of claim 8, wherein the second electrode includes an electrically conductive snare loop.

12. The method of claim 11, further including tightening the electrically conductive snare loop around the targeted tissue.

13. The method of claim 8, wherein the injected fluid is an electrically conductive fluid.

14. A method of resecting targeted tissue, comprising:
   inserting a first electrically conductive snare within the targeted tissue;
   extending a second electrically conductive snare distally of an injection needle housed within a catheter, wherein the injection needle includes an insulation coating;
   passing current between the first electrically conductive snare and the second electrically conductive snare;
   adjusting an amount of the current passed between the first and second electrically conductive snares by moving at least one of the first or second snares relative to another of the first or second electrically conductive snares;
   aligning an alignment mechanism of the first electrically conductive snare relative to an alignment mechanism of the second electrically conductive snare; and
   resecting the targeted tissue via the first and second electrically conductive snares.

15. The method of claim 14, wherein the targeted tissue is submucosal tissue.

16. The method of claim 14, further including tightening at least one of the first and second snares around the target tissue.

17. The method of claim 14, wherein the first and second electrically conductive snares form a bipolar circuit.

* * * * *